US008182791B2

(12) United States Patent
Staniforth et al.

(10) Patent No.: US 8,182,791 B2
(45) Date of Patent: May 22, 2012

(54) FORMULATIONS FOR USE IN INHALER DEVICES

(75) Inventors: John Nicholas Staniforth, Bath (GB); David Alexander Vodden Morton, Bath (GB); Rajbir Gill, Wiltshire (GB); Gaetano Brambilla, Parma (IT); Rossella Musa, Parma (IT); Lorenzo Ferrarini, Parma (IT)

(73) Assignee: Vectura Limited, Chippenham (GB)

( * ) Notice: Subject to any disclaimer, the term of this patent is extended or adjusted under 35 U.S.C. 154(b) by 0 days.

(21) Appl. No.: 10/257,790

(22) PCT Filed: Apr. 17, 2001

(86) PCT No.: PCT/GB01/01732
§ 371 (c)(1),
(2), (4) Date: May 5, 2003

(87) PCT Pub. No.: WO01/78694
PCT Pub. Date: Oct. 25, 2001

(65) Prior Publication Data
US 2003/0175214 A1 Sep. 18, 2003

(30) Foreign Application Priority Data

Apr. 17, 2000 (GB) .................................. 0009469.8
Jun. 27, 2000 (EP) ..................................... 00113608

(51) Int. Cl.
*A61K 9/12* (2006.01)
*A61K 9/14* (2006.01)
*A61K 9/16* (2006.01)
*A61M 11/00* (2006.01)

(52) U.S. Cl. ............ 424/45; 424/46; 424/489; 424/490; 424/499; 128/200.14; 128/203.15; 514/2

(58) Field of Classification Search .................... 424/45, 424/46, 489, 490, 499, 450; 128/200.14, 128/203.15; 514/2, 561
See application file for complete search history.

(56) References Cited

U.S. PATENT DOCUMENTS

| | | | | |
|---|---|---|---|---|
| 5,376,386 A | * | 12/1994 | Ganderton et al. | ............ 424/499 |
| 6,153,224 A | * | 11/2000 | Staniforth | ..................... 424/490 |
| 6,475,462 B1 | * | 11/2002 | Dodson et al. | ................. 423/659 |
| 6,518,239 B1 | * | 2/2003 | Kuo et al. | ............................ 514/2 |
| 6,521,260 B1 | * | 2/2003 | Staniforth | ..................... 424/490 |
| 6,528,096 B1 | * | 3/2003 | Musa et al. | ..................... 424/490 |
| 6,655,379 B2 | * | 12/2003 | Clark et al. | ............... 128/203.12 |
| 7,541,022 B2 | * | 6/2009 | Staniforth et al. | ............... 424/46 |
| 7,744,855 B2 | * | 6/2010 | Staniforth et al. | ............... 424/45 |
| 2003/0162835 A1 | * | 8/2003 | Staniforth et al. | ............. 514/561 |
| 2003/0165436 A1 | * | 9/2003 | Staniforth et al. | ............... 424/46 |
| 2003/0180227 A1 | * | 9/2003 | Staniforth et al. | ............... 424/46 |
| 2003/0185764 A1 | * | 10/2003 | Staniforth et al. | ............... 424/46 |

FOREIGN PATENT DOCUMENTS

| | | |
|---|---|---|
| GB | 2269992 | 3/1994 |
| WO | WO 9311746 | 12/1992 |
| WO | WO 9511666 | 10/1994 |
| WO | WO 9602231 | 6/1995 |
| WO | WO 9623485 | 1/1996 |
| WO | WO 9703649 | 7/1996 |
| WO | WO 0028979 | 11/1999 |

OTHER PUBLICATIONS

Lucas P. et al., "Protein Deposition from Dry Powder Inhalers: Fine Particle Multiplets as Performance Modifiers." Pharm. Research, vol. 15, No. 4; Apr. 1998 pp. 562-569.
Kawashima Y. et al, "Effect of Surface Morphology of Carrier Lactose on Dry Powder Inhalation Property of Pranlukast Hydrate." International Journalof Pharmaceutics, vol. 172, No. 1-2; Oct. 15, 1998 pp. 179-188.
Ganderton, D. "The Generation of Respirable Clouds Form Coarse Powder Aggregates," Journal of Biopharmaceutical Sciences, 3(1/2), pp. 101-105 (1992).
Kassem, N.M., "Generation of Deeply Inspirable Clouds from Dry Powder Aggregates," Department of Pharmacy, King's College, University of London, Thesis No. DX187842 (1990).
Zeng et al., "Particulate Interactions in Dry Powder Formulations for Inhalation," Department of Pharmacy, King's College London, Taylor & Francis, Inc., pp. 88-90 (2001).
Zeng et al., "Particulate Interactions in Dry Powder Formulations for Inhalation," Department of Pharmacy, King's College London, Taylor & Francis, Inc., Chapter 2, pp. 31-64 (2001).

* cited by examiner

*Primary Examiner* — Mina Haghighatian
(74) *Attorney, Agent, or Firm* — Davidson, Davidson & Kappel, LLC

(57) ABSTRACT

A formulation for an inhaler device comprises carrier particles having a diameter of at least 50 μm and a mass median diameter of at least 175 μm; active particles; and additive material to which is able to promote release of the active particles from the carrier particles on actuation of the inhaler device. The formulation has excellent flowability even at relatively high fine particle contents.

63 Claims, 4 Drawing Sheets

FORMULATIONS FOR USE IN INHALER DEVICES

Figure 1:
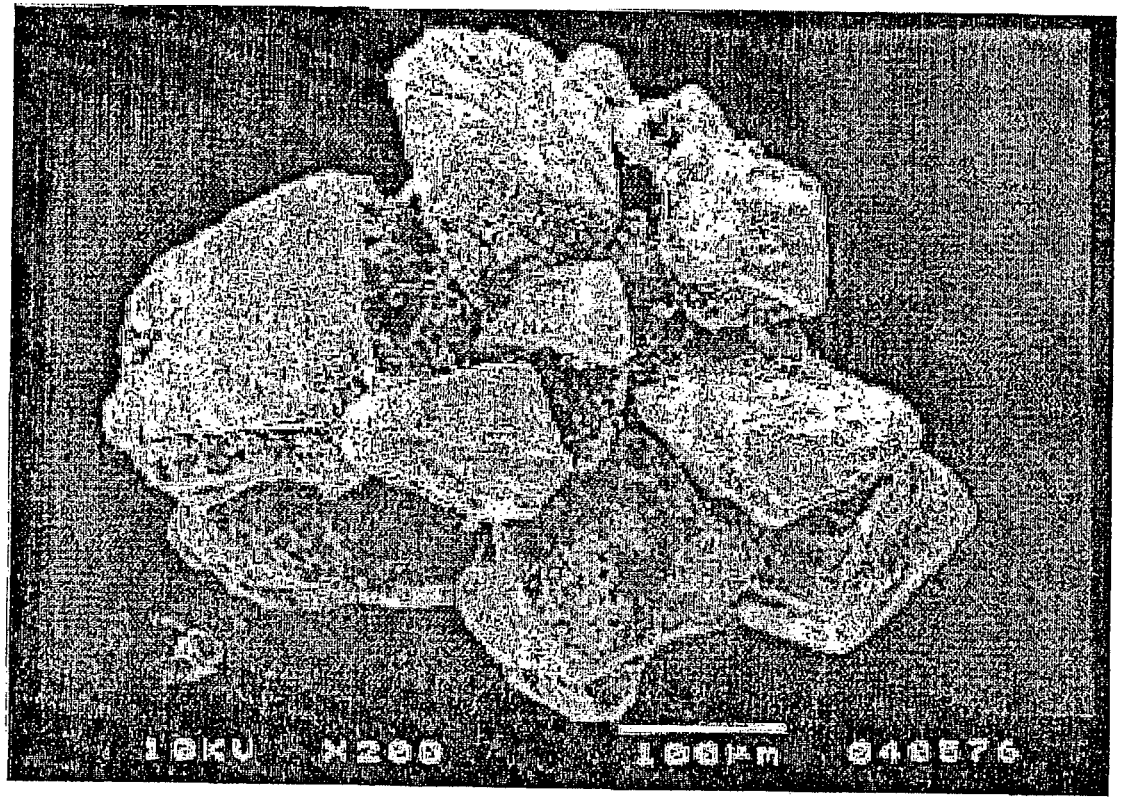
Figure 2:
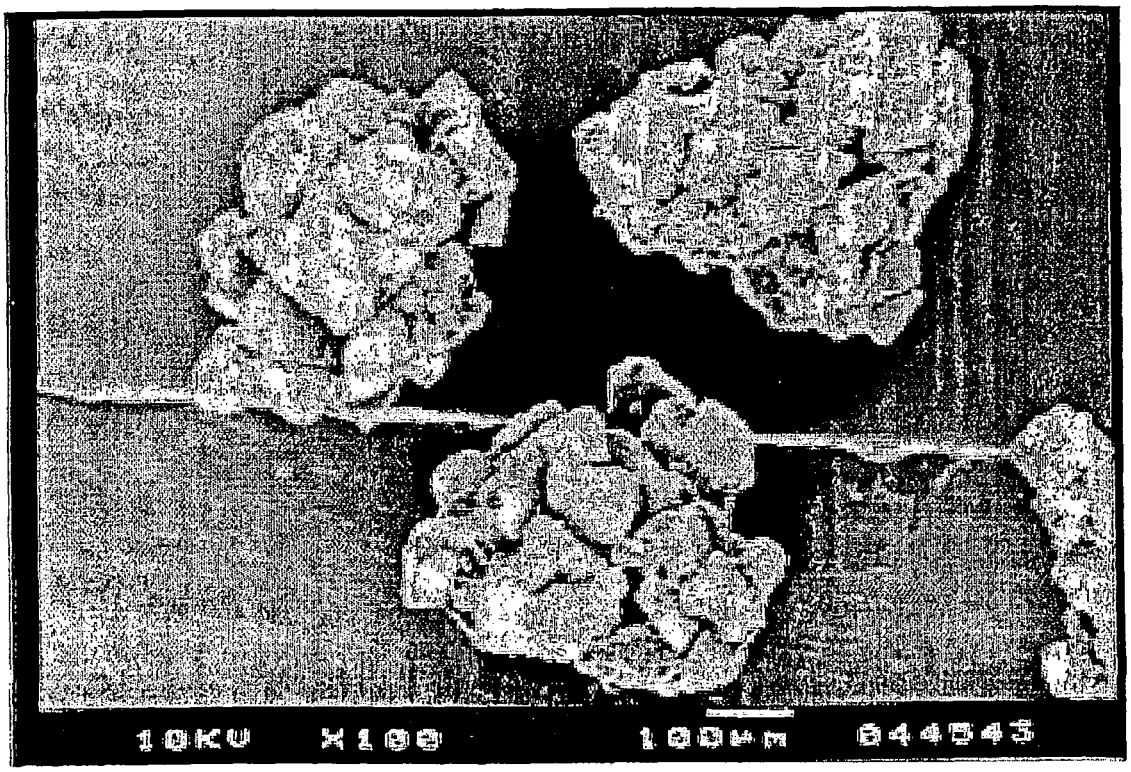
Figure 3:
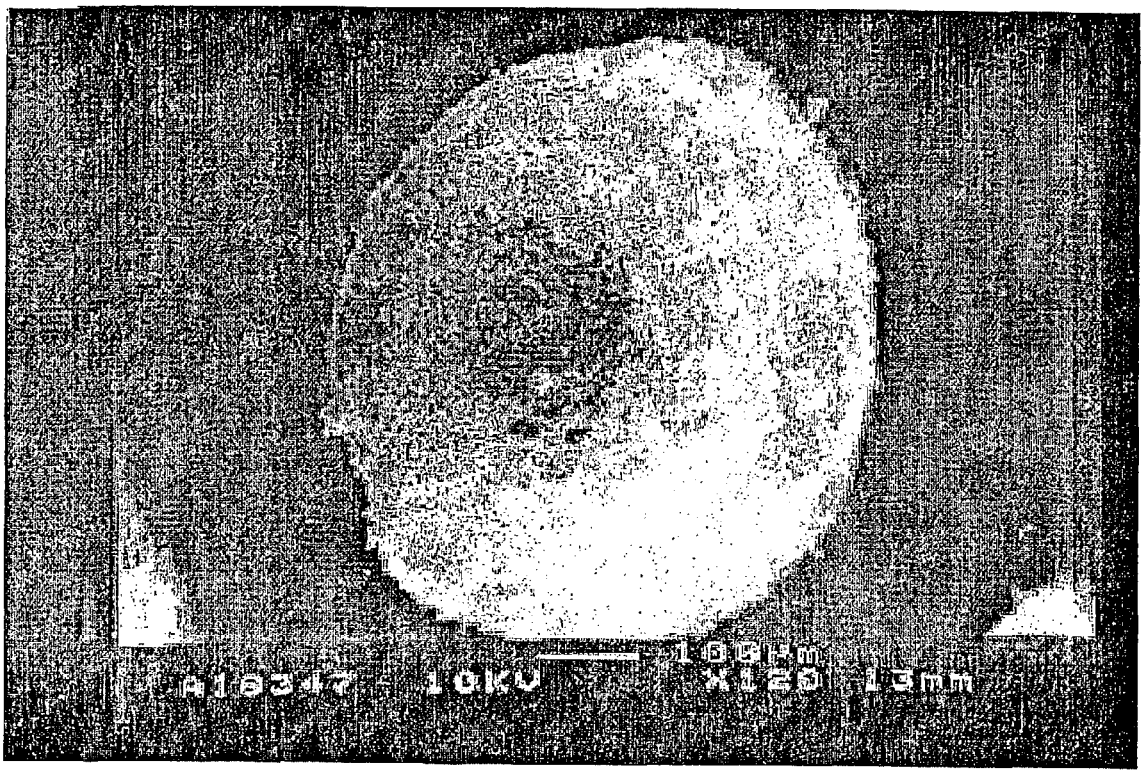
Figure 4:
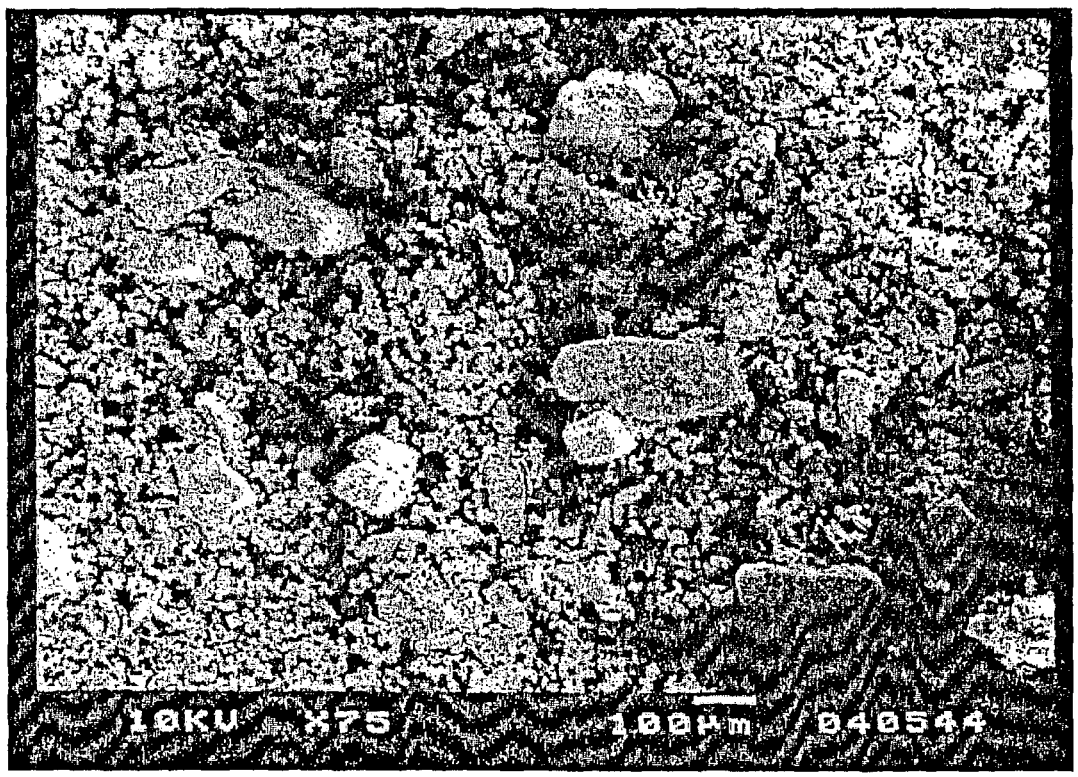

The invention relates to carrier materials for use in inhaler devices, to formulations comprising the carrier materials and to the use of the formulations.

The administration of pharmacologically active agents by inhalation is a widely used technique, especially for the treatment of diseases of the respiratory tract. The technique is also used for the administration of certain active agents having systemic action, which are absorbed, via the lungs, into the bloodstream. Known inhaler devices include nebulizers, pressurised metered dose inhalers and dry powder inhalers. The present invention is primarily concerned with formulations for use in dry powder inhalers, although in some circumstances formulations according to this invention may also or instead be useful in pressurised metered dose inhalers.

The delivery of dry powder particles of an active agent to the respiratory tract presents certain problems. The inhaler should deliver to the lungs the maximum possible proportion of the active particles expelled from the device, including a significant proportion to the lower lung, preferably even at the poor inhalation capabilities of some patients, especially asthmatics. In use of many of the currently available devices, however, only a proportion, and frequently as little as 10%, of the active particles expelled from the device on inhalation reach the lower lung.

On exit from the inhaler device, the active particles should form a physically and chemically stable aerocolloid which remains in suspension until it reaches an alveolar or other absorption site. Once at the absorption site, the active particles should be capable of efficient collection by the pulmonary mucosa with no active particles being exhaled from the absorption site.

The size of the active particles is important. For effective delivery of active particles deep into the lungs, the active particles should be small, with an equivalent aerodynamic diameter substantially in the range of up to 10 µm. Small particles are however thermodynamically unstable due to their high surface area to volume ratio, which provides significant excess surface free energy and encourages particles to agglomerate. Agglomeration of small particles in the inhaler and adherence of particles to the walls of the inhaler can result in the active particles leaving the inhaler as large agglomerates or in their not leaving the inhaler and remaining adhered to the interior thereof.

The uncertainty as to the extent of agglomeration of the particles between each actuation of the inhaler and between different inhalers and different batches of particles, leads to poor dose reproducibility. It has been found that powders are generally reproducibly fluidisable, and therefore reliably removable from an inhaler device, when the particles have a diameter greater than 60 µm. Good flow properties are desirable in the contexts of metering and of dispersal from the device.

To give the most effective dry powder aerosol, therefore, the particles should be large while in the inhalers, but small when in the respiratory tract.

It is common, in an attempt to achieve those demands, to include in the dry powder formulation carrier particles, to which the active particles can adhere whilst in the device, the active particles then being dispersed from the surfaces of the carrier particles on inhalation into the respiratory tract, to give a fine suspension. It is known that the presence of a certain amount of fine excipient material, normally of the same material as the carrier, can improve the proportion of drug reaching the lung. The presence of such a fraction of fine excipient is conventionally limited to less than 10% and generally less than 5% due to the catastrophic loss of flowability at higher fine particle contents, leading to poor dose reproducibility.

The proportion of the active particles reaching the lung can be increased by incorporating in the formulation an agent which promotes release of the active particle, as described in WO96/23485.

The invention provides a formulation for use in an inhaler device, comprising
- carrier particles having a diameter of at least 50 µm and a mass median diameter of at least 175 µm;
- active particles; and
- additive material which is able to promote release of the active particles from the carrier particles on actuation of the inhaler device.

The formulation of the invention surprisingly has both excellent flowability within the device and, on expulsion from the device, permits good dispersion of the active particles from the carrier particles and generation of a relatively high fine particle fraction, promoting delivery of a relatively large proportion of the active particles into the lung.

The use of carrier particles of relatively large size is described in WO96/02231, but that document does not suggest the incorporation of additive material to promote release of the active particles from the carrier particles. The carrier particles used in accordance with the present invention have a mass median diameter (MMD) of at least 175 µm. In fact, it is preferred that the MMD of the carrier particles is at least 200 µm, and more preferably at least 250 µm.

The carrier particles have a diameter of at least 50 µm. Although as described below the formulation may include particles of diameter less than 50 µm of the same material as the carrier particles, those smaller particles are not included within the term "carrier particles" as used herein. Advantageously, not more than 10% by weight, and preferably not more than 5% by weight, of the carrier particles have a diameter of 150 µm or less. Advantageously at least 90% by weight of the carrier particles have a diameter of 175 µm or more, and preferably 200 µm or more. Advantageously, at least 90% by weight, and preferably at least 95% by weight, of the carrier particles have a diameter of not more than 1 mm. Preferably at least 90% by weight of the carrier particles have a diameter of not more than 600 µm. Advantageously, at least 50% by weight, and preferably at least 60% by weight, of the carrier particles have a diameter of 200 µm or more. Preferably, at least 90% by weight of the carrier particles have a diameter between 150 µm and 750 µm, more preferably between 150 µm and 650 µm. Particular advantages are offered by formulations in which substantially all of the carrier particles have a diameter in the range of about 210 to about 360 µm or from about 350 to about 600 µm.

The carrier particles may be of any acceptable pharmacologically inert material or combination of materials. For example, the carrier particles may be composed of one or more materials selected from sugar alcohols; polyols, for example sorbitol, mannitol and xylitol, and crystalline sugars, including monosaccharides and disaccharides; inorganic salts such as sodium chloride and calcium carbonate; organic salts such as sodium lactate; and other organic compounds such as urea, polysaccharides, for example starch and its derivatives; oligosaccharides, for example cyclodextrins and dextrins. Advantageously the carrier particles are of a crystalline sugar, for example, a monosaccharide such as glucose or arabinose, or a disaccharide such as maltose, saccharose, dextrose or lactose. Preferably, the carrier particles are of lactose.

The carrier particles are preferably of a material having a fissured surface, that is, on which there are clefts and valleys and other recessed regions, referred to herein collectively as fissures. The fissures should preferably be a least 5 µm wide extending to at least 5 µm deep, preferably at least 10 µm wide and 10 µm deep and most preferably at least 20 µm wide and 20 µm deep.

Because of the excellent flow properties of the formulations containing the fissured carrier particles, the formulations offer special advantages in the administration of active agents to be administered in relatively large doses. Thus, whereas formulations containing conventional lactose carriers and fine particle contents of above 5% tend to have poor flow properties, with flow properties at fine particle contents above 10% being very poor, the formulations of the invention may have adequate flow properties even at fines contents (that is contents of active particles and of any fine particles of additive material, together with any other particles of aerodynamic diameter of not more than 20 µm) of up to 90% by weight, based on the total weight of fines and carrier particles. Moreover, the fissured carrier particles offer particular advantages in that they are capable of retaining relatively large amounts of fine material in the fissures without or with only little segregation. That is thought to underly the good respirable fraction that is generated in use of the formulations and is especially advantageous in use of the carrier particles with certain additive materials, for example, magnesium stearate, which tend to cause segregation of the components, permitting increased amounts of such additive materials to be used without increasing segregation to unacceptable levels. Advantageously, the fines content is not more than 50% by weight, and more preferably not more than 20% by weight, based on the total weight of fines and carrier particles. Preferably, the fines content is at least 5% by weight, based on the total weight of fines and carrier particles. The invention offers particular advantages in the case of formulations containing at least 10%, for example, from 10 to 20% by weight fines or at least 20%, for example from 20 to 50% by weight fines, in each case, based on the total weight of fines and carrier particles. The fines content may include from 0.1 to 99% by weight active particles, for example from 0.1 to 90% by weight, and advantageously from 0.1 to 80% by weight active particles, in each case based on the total weight of fines. In many cases, however, the active particles will constitute less than half of the total weight of fines.

A number of methods may be used to determine whether carrier particles have a fissured surface that will offer the above-mentioned capability of retaining relatively large fines contents substantially without segregation:

1. Determination of Tapped Density.

The tapped density of the fissured carrier particles may be about 6% or more, and preferably 15% or more, lower than the tapped density of carrier particles of the same material and of particle characteristics of a kind typical of carrier particles which have conventionally been used in the manufacture of inhalable powders. In the case of fissured carrier particles of crystalline sugars, for example lactose, the tapped density of the fissured particles is not more than 0.75 g/cm$^3$, and preferably not more than 0.70 g/cm$^3$. The tapped density of lactose grades conventionally used in the manufacture of commercial DPI formulations is typically about 0.8 g/cm$^3$. Tapped densities referred to herein may be measured as follows:

A measuring cylinder is weighed on a top pan balance (2 place). Approximately 50 g powder is introduced into the measuring cylinder, and the weight is recorded. The measuring cylinder containing the powder is attached to a jolting volumeter (Jel Stampfvolumeter). The jolting volumeter is set to tap 200 times. During each tap, the measuring cylinder is raised and allowed to fall a set distance. After the 200 taps, the volume of the powder is measured. The tapping is repeated and the new volume measured. The tapping is continued until the powder will settle no more. The tapped density is calculated as the weight of the powder divided by the final tap volume. The procedure is performed three times (with new powder each time) for each powder measured, and the mean tapped density calculated from those three final tapped volume values.

2. Mercury Intrusion Porosimetry. Mercury intrusion porosimetry assesses the pore size distribution and the nature of the surface and pore structure of the particles. Porosimetry data is suitably collected over pressure range, 3.2 kPa to 8.7 MPa, for example, using an Autopore 9200 II Porosimeter (Micromeritics, Norcross, USA). Samples should be evacuated to below 5 Pa prior to analysis to remove air and loosely bound surface water. Suitable lactose is characterised by a bulk density of not more than 0.65 g/cm$^3$ and preferably not more than 0.6 g/cm$^3$. Suitable lactose is also characterised by a total intrusion volume measured by mercury intrusion porosimetry of at least 0.8 cm$^3$ g$^{-1}$ and preferably at least, 0.9 cm$^3$ g$^{-1}$. (It has been found that lactose having a bulk density of 0.6 g/cm$^3$ as measured by mercury intrusion porosimetry has a tapped density of about 0.7 g/cm$^3$, whereas the discrepancy between the two methods at lower densities is less.)

3. "Fissure Index". The term "fissure index" used herein refers to the ratio of a theoretical envelope volume of the particles, as calculated from the envelope of the particles, to the actual volume of the particles, that is, omitting fissures within the envelope. Suitable particles are those having a fissure index of at least 1.25. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. The Feret's diameter for particles within a grid is measured relative to a fixed axis of the image. Typically at least ten particles are measured for their Feret's diameter. Feret's diameter is defined as the length of the projection of a particle along a given reference line as the distance between the extreme left and right tangents that are perpendicular to the reference line. A mean Feret's diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. First, the mean mass of a particle is calculated. A sample of approximately 50 mg is taken and its precise weight recorded to 0.1 mg. Then by optical microscopy the precise number of particles in that sample is determined. The mean mass of one particle can then be determined. The procedure is then repeated five times to obtain a mean value of this mean. Second, a fixed mass of particles (typically 50 g), is weighed out accurately, and the number of particles within this mass is calculated using the above mean mass value of one particle. Finally, the sample of particles is immersed in a liquid in which the particles are insoluble and, after agitation to remove trapped air, the amount of liquid displaced is measured. From this the mean actual volume of one particle can be calculated. The fissure index is advantageously not less than 1.5, and is, for example, 2 or more.

4. "Rugosity Coefficient". The rugosity coefficient is used to mean the ratio of the perimeter of a particle outline to the perimeter of the 'convex hull'. This measure has been used to express the lack of smoothness in the particle outline. The 'convex hull' is defined as a minimum enveloping boundary fitted to a particle outline that is nowhere concave. (See "The Shape of Powder-Particle Outlines" A. E. Hawkins, Wiley.) The 'rugosity coefficient' may be calculated optically as follows. A sample of particles should be identified from an electron micrograph as identified above. For each particle the perimeter of the particle outline and the associated perimeter of the 'convex hull' is measured to provide the rugosity coefficient. This should be repeated for at least ten particles to obtain a mean value. The mean rugosity coefficient is at least 1.25.

Carrier particles which have the above-mentioned capability of retaining relatively large amounts of fine material without or with only little segregation will generally comply with all of Methods 1 to 4 above, but for the avoidance of doubt any carrier particles which comply with at least one of Methods 1 to 4 is deemed to be a fissured particle.

The carrier particles are advantageously in the form of an agglomerate consisting of a plurality of crystals fused to one another, the fastness of agglomeration being such that the carrier particles have substantially no tendency to disintegrate on expulsion from the inhaler device. In the case of crystalline sugars, such as lactose, such structures may be obtained in a wet granulation process, in which crystals within an agglomerate become fused to one another by solid bridges, the resultant structure having a complex shape of high irregularity and/or high fractal dimension, including a multiplicity of clefts and valleys, which in some cases may be relatively deep. Each agglomerate will generally contain at least three lactose primary crystals of the characteristic tomahawk shape.

Such agglomerates are clearly distinguished from agglomerates of the kind which form in powder formulations by aggregation of particles, which do tend to disintegrate on expulsion from the inhaler.

Suitably shaped carrier particles also include dendritic spherulites of the type disclosed in U.S. Pat. No. 4,349,542 for use in table manufacture.

The carrier particles advantageously constitute at least 50%, preferably at least 60% and especially at least 70% by weight of the formulation, based on the total weight of the formulation.

The additive material, which is preferably on the surfaces of the carrier particles, promotes the release of the active particles from the carrier particles on actuation of the inhaler device. The formulation containing the additive material should, however, be such that the active particles are not liable to be released form the carrier particles before actuation of the inhaler device. The additive material, which it will be appreciated is of a different material from the carrier particles, may be in the form of particles, the additive particles being attached to the surfaces of the carrier particles.

In International Specification WO 96/23485 many examples are given of additive materials which are such that the active particles are not liable to be released from the carrier particles before actuation of the inhaler device but are released during use of the inhaler device. "Actuation of the inhaler device" refers to the process during which a dose of the powder is removed from its rest position in the inhaler device, usually by a patient inhaling. That step takes place after the powder has been loaded into the inhaler device ready for use.

If it is desired to test whether or not the active particles of a powder are liable to be released from the carrier particles before actuation of the inhaler device a test can be carried out. A suitable test is described in International Specification WO96/23485 (Example 12 and 13). A powder whose post-vibration homogeneity measured as a percentage coefficient of variation, after being subjected to the described test, is less than about 5% can be regarded as acceptable.

It is believed that additive material is attracted to and adheres to high energy sites on the surfaces of the carrier particles on introduction of the active particles, many of the high energy sites are now occupied, and the active particles therefore occupy the lower energy sites on the surfaces of the carrier particles. That results in the easier and more efficient release of the active particles in the air stream created on inhalation, thereby giving increased deposition of the active particles in the lungs.

However, as indicated above, it has been found that the addition of more than a small amount of additive material can be disadvantageous because of the adverse effect on the ability to process the mix during commercial manufacture.

It is also advantageous for as little as possible of the additive material to reach the lungs on inhalation of the powder. Although the additive material will most advantageously be one that is safe to inhale into the lungs, it is still preferred that only a very small proportion, if any, of the additive material reaches the lung, in particular the lower lung. The considerations that apply when selecting the additive material and other features of the powder are therefore different from the considerations when a third component is added to carrier and active material for certain other reasons, for example to improve absorption of the active material in the lung, in which case it would of course be advantageous for as much as possible of the additive material in the powder to reach the lung.

The optimum amount of additive material will depend on the chemical composition and other properties of the additive material. In general, the amount of additive will be not more than 50% by weight, based on the total weight of the formulations. However, it is thought that for most additives the amount of additive material should be not more than 10%, more advantageously not more than 5%, preferably not more than 4% and for most materials will be not more than 2% or even not more than 1% by weight or not more than 0.25% based on the total weight of the formulation. In general, the amount of additive material is at least 0.01% by weight based on the total weight of the formulation.

Advantageously the additive material is an anti-adherent material and will tend to decrease the cohesion between the anti-adherent materials and the carrier particles. In order to determine whether a given material is an anti-adherent material, the test described in International Specification WO97/03649 (pages 6 and 7) using an "Aeroflow" apparatus may be used, anti-adherent materials being those additive materials that result in a lowering of the mean time between avalanches of the powder, as compared with the powder in the absence of the additive material.

Advantageously the additive material is an anti-friction agent (glidant) and will give better flow of powder in the dry powder inhaler which will lead to a better dose reproducibility from the inhaler device.

Where reference is made to an anti-adherent material, or to an anti-friction agent, the reference is to include those materials which will tend to decrease the cohesion between the active particles and the carrier particles, or which will tend to improve the flow of powder in the inhaler, even though they may not usually be referred to as anti-adherent material or an anti-friction agent. For example, leucine is an anti-adherent material as herein defined and is generally thought of as an anti-adherent material but lecithin is also an anti-adherent material as herein defined, even though it is not generally though of as being anti-adherent, because it will tend to decrease the cohesion between the active particles and the carrier particles. Advantageously, the additive material consists of physiologically acceptable material. As already indicated, it is preferable for only small amounts of additive material to reach the lower lung, and it is also highly preferable for the additive material to be a material which may be safely inhaled into the lower lung where it may be absorbed into the blood stream. That is especially important where the additive material is in the form of particles.

The additive material may include a combination of one or more materials.

It will be appreciated that the chemical composition of the additive material is of particular importance.

It will furthermore be appreciated that additive materials that are naturally occurring animal or plant substances will offer certain advantages.

Advantageously, the additive material includes one or more compounds selected from amino acids and derivatives thereof, and peptides and polypeptides having molecular weight from 0.25 to 100 Kda, and derivatives thereof. Amino acids, peptides or polypeptides and their derivatives are both physiologically acceptable and give acceptable release of the active particles on inhalation.

It is particularly advantageous for the additive material to comprise an amino acid. Amino acids have been found to give, when present in low amounts in a powder as additive material, high respirable fraction of the active materials with little segregation of the powder and also with very little of the amino acid being transported into the lower lung. In respect of leucine, a preferred amino acid, it is found that, for example, for an average dose of powder only about 10 μg of leucine would reach the lower lung. The additive material may comprise one or more of any of the following amino acids: leucine, isoleucine, lysine, valine, methionine, phenylalanine. The additive may be a salt of a derivative of an amino acid, for example aspartame or acesulfame K. Preferably, the additive particles consist substantially of leucine, advantageously L-leucine. As indicated above, leucine has been found to give particularly efficient release of the active particles on inhalation. Whilst the L-form of an amino acid is used in Examples described below, the D- and DL-forms may also be used.

Additive materials which comprise one or more water soluble substances offer certain advantages. This helps absorption of the substance by the body if the additive reaches the lower lung. The additive material may include dipolar ions, which may consist of zwitterions.

Alternatively, the additive material may comprise particles of a phospholipid or a derivative thereof. Lecithin has been found to be a good material for the additive material.

The additive material may include or consist of one or more surface active materials, in particular materials that are surface active in the solid state, which may be water soluble, for example lecithin, in particular soya lecithin, or substantially water insoluble, for example solid state fatty acids such as lauric acid, palmitic acid, stearic acid, erucic acid, behenic acid, or derivatives (such as esters and salts) thereof. Specific examples of such materials are: magnesium stearate; sodium stearyl fumarate; sodium stearyl lactylate; phospatidylcholines, phosphatidylglycerols and other examples of natural and synthetic lung surfactants; liposomal formulations; lauric acid and its salts, for example, sodium lauryl sulphate, magnesium lauryl sulphate; triglycerides such as Dynsan 118 and Cutina HR; and sugar esters in general.

Other possible additive materials include talc, titanium dioxide, aluminium dioxide, silicon dioxide and starch.

The expression "additive material" as used herein does not include crystalline sugars. Whereas small particles of one or more crystalline sugars may be present, and are indeed preferred to be present, as described below, formulations which contain small crystalline sugar particles will also contain a further substance which is an additive material in the sense in which that expression is used herein.

In the case of certain additive materials, it is important for the additive material to be added in a small amount. For example, magnesium stearate is highly surface active and should therefore be added in small amounts, for example, up to 2.5%, by weight based on the weight of the formulation with amounts of from 0.1 to 2% being preferred, for example, 0.5% to 1.7% especially 0.75 to 1.5% by weight. In some cases, it might be found advantageous to use smaller amounts of magnesium stearate, for example, from 0.02 to 0.6%, or 0.2 to 0.4% by weight. Phosphatidylcholines and phosphatidylgycerols on the other hand are less active and can usefully be added in greater amounts. In respect of leucine, which is still less active, an addition of 2% by weight leucine based on the weight of the powder gives good results in respect of the respirable fraction of the active particles, low segregation and low amount of leucine reaching the lower lung; it is explained in WO 96/23485 that an addition of a greater amount does not improve the results and in particular does not significantly improve the respirable fraction and therefore whilst even with 6% leucine a reasonable result is obtained that is not preferred since it results in an increased quantity of additive material being taken into the body and will adversely affect the processing properties of the mix. In the preferred formulations of the present invention using fissured carrier particles, however, it has been found that increased amounts of additive material may be used and give improved respirable fractions.

The additive material will often be added in particulate form but it may be added in liquid or solid form and for some materials, especially where it may not be easy to form particles of the material and/or where those particles should be especially small, it may be preferred to add the material in a liquid, for example as a suspension or a solution or as a melt. Even then, however, the additive material of the finished powder may be in particulate form. An alternative possibility, however, that is within the scope of the invention is to use an additive material which remains liquid even in the final essentially particulate material which can still be described as a "dry powder".

In some cases improved clinical benefits will be obtained where the additive material is not in the form of particles of material. In particular, the additive material is less likely to leave the surface of the carrier particle and be transported into the lower lung.

Where the additive material of the finished powder is particulate, the nature of the particles may be significant. The additive particles may be non-spherical in shape. Advantageously, the additive particles are plate-like particles. Alternatively, the additive particles may be angular for example prisms, or dendritic in shape. Additive particles which are non-spherical may be easier to remove from the surfaces of the carrier particles than spherical, non-angular particles and plate-like particles may give improved surface interaction and glidant action between the carrier particles.

The surface area of the additive particles is also thought to be important. The surface area of the additive particles, as measured using gas absorption techniques, is preferably at least 5 m$^2$ g$^{-1}$. In many cases it is found that additive material comprising small plate-like particles is preferred.

Advantageously, at least 90% by weight of the additive particles have an aerodynamic diameter less than 150 µm, more advantageously less than 100 μm, preferably less than 50 μm. Advantageously, the MMAD of the additive particles is not more than 20 μm, preferably not more than 15 μm, and more preferably not more than 10 μm. The additive particles preferably have a mass median diameter less than the mass median diameter of the carrier particles and will usually have a mass median diameter of approximately between a tenth and a thousandth, for example, between a fiftieth and a five hundredth that of the carrier particles. The MMAD of the additive particles will generally be not less than 0.1 μm, for example, not less than 1 μm.

The amount of additive material will depend upon the nature of the additive material, and will generally be at least 0.01% based on the weight of the carrier particles. In the case of additive materials that do not tend to segregate from the carrier particles, the additive material may be present in amounts of up to 50%, by weight, based on the weight of the carrier particles and additive. Advantageously, the additive material may constitute up to one third of the combined weight of additive and carrier particles. In general, the amount of additive material will not exceed 10%, and preferably not exceed 5%, of the combined weight of additive and carrier particles.

In the use of those additive materials which do have a tendency to segregate, the amount of additive material will generally be less than 5%, for example not more than 3% by weight based on the combined weight of additive material and carrier particles.

The active particles referred to throughout the specification will comprise an effective amount of at least one active agent that has therapeutic activity when delivered into the lung. The active particles advantageously consist essentially of one or more therapeutically active agents. Suitable therapeutically active agents may be drugs for therapeutic and/or prophylactic use. Active agents which may be included in the formulation include those products which are usually administered orally by inhalation for the treatment of disease such a respiratory disease, for example, β-agonists.

The active particles may comprise at least one $\beta_2$-agonist, for example one or more compounds selected from terbutaline, salbutamol, salmeterol and formoterol. If desired, the active particles may comprise more than one of those active agents, provided that they are compatible with one another under conditions of storage and use.

Preferably, the active particles are particles of salbutamol sulphate. References herein to any active agent are to be understood to include any physiologically acceptable derivative. In the case of the $\beta_2$-agonists mentioned above, physiologically acceptable derivatives include especially salts, including sulphates.

The active particles may be particles of ipatropium bromide.

The active particles may include a steroid, which may be beclometasone dipropionate or may be fluticasone. The active principle may include a cromone which may be sodium cromoglycate or nedocromil. The active principle may include a leukotriene receptor antagonist.

The active particles may include a carbohydrate, for example heparin.

The active particles may advantageously comprise a therapeutically active agent for systemic use provided that that agent is capable of being absorbed into the circulatory system via the lungs. For example, the active particles may comprise peptides or polypeptides or proteins such as DNase, leukotrienes or insulin (including substituted insulins and pro-insulins), cyclosporin, interleukins, cytokines, anti-cytokines and cytokine receptors, vaccines (including influenza, measles, 'anti-narcotic' antibodies, meningitis), growth hormone, leuprolide and related analogues, interferons, desmopressin, immunoglobulins, erythropoeitin, calcitonin and parathyroid hormone. The formulation of the invention may in particular have application in the administration of insulin to diabetic patients, thus avoiding the normally invasive administration techniques used for that agent.

The formulations of the invention may advantageously be for use in pain relief. Non-opioid analgesic agents that may be included as pain relief agents are, for example, alprazolam, amitriptyline, aspirin, baclofen, benzodiazepines, bisphosphonates, caffeine, calcitonin, calcium-regulating agents, carbamazepine, clonidine, corticosteroids, dantrolene, dexamethasone, disodium pamidronate, ergotamine, flecainide, hydroxyzine, hyoscine, ibuprofen, ketamine, lignocaine, lorazepam, methotrimeprazine, methylprednisolone, mexiletine, mianserin, midazolam, NSAIDs, nimodipine, octreotide, paracetamol, phenothiazines, prednisolone, somatostatin. Suitable opioid analgesic agents are: alfentanil hydrochloride, alphaprodine hydrochloride, anileridine, bezitramide, buprenorphine hydrochloride, butorphanol tartrate, carfentanil citrate, ciramadol, codeine, dextromoramide, dextropropoxyphene, dezocine, diamorphine hydrochloride, dihydrocodeine, dipipanone hydrochloride, enadoline, eptazocine hydrobromide, ethoheptazine citrate, ethylmorphine hydrochloride, etorphine hydrochloride, fentanyl citrate, hydrocodone, hydromorphone hydrochloride, ketobemidone, levomethadone hydrochloride, levomethadyl acetate, levorphanol tartrate, meptazinol hydrochloride, methadone hydrochloride, morphine, nalbuphine hydrochloride, nicomorphine hydrochloride, opium, hydrochlorides of mixed opium alkaloids, papaveretum, oxycodone, oxymorphone hydrochloride, pentamorphone, pentazocine, pethidine hydrochloride, phenazocine hydrobromide, phenoperidine hydrochloride, picenadol hydrochloride, piritramide, propiram fumarate, remifentanil hydrochloride, spiradoline mesylate, sufentanil citrate, tilidate hydrochloride, tonazocine mesylate, tramadol hydrochloride, trefentanil.

The technique could also be used for the local administration of other agents for example for anti cancer activity, anti-virals, antibiotics, muscle relaxants, antidepressants, antiepileptics or the local delivery of vaccines to the respiratory tract.

The active particles advantageously have a mass median aerodynamic diameter in the range of up to 15 μm, for example from 0.01 to 15 μm, preferably from 0.1 to 10 μm, for example, from 1 to 8 μm. Most preferably, the mass median aerodynamic diameter of the active particles is not exceeding 5 μm. The active particles are present in an effective amount, for example, at least 0.01% by weight, and may be present in an amount of up to 90% by weight based on the total weight of carrier particles, additive materials and active particles. Advantageously, the active particles are present in an amount not exceeding 60% by weight based on the total weight of carrier particles, additive particles and active particles.

It will be appreciated that the proportion of active agent present will be chosen according to the nature of the active agent. In many cases, it will be preferred for the active agent to constitute no more than 10%, more preferably no more than 5%, and especially no more than 2% by weight based on the total weight of carrier particles, additive particles and active particles.

The formulation may further comprise fine particles of an excipient material, that is to say, particles of aerodynamic diameter not more than 50 µm, of a substantially inert pharmacologically acceptable material. The excipient material may be any substantially inert material that is suitable for use as an excipient in an inhalable formulation. The excipient material preferably comprises one or more crystalline sugars, for example, dextrose and/or lactose. Most preferably the excipient material consists essentially of lactose.

Advantageously, the fine excipient particles are of the same material as the carrier particles. It is especially preferred for the carrier particles and the fine excipient particles to be of lactose.

Advantageously, at least 90% by weight of the fine excipient particles have an aerodynamic diameter of not more than 40 μm. The fine excipient particles advantageously have an MMAD of not more than 20 μm, preferably not more than 15 μm, more preferably not more than 10 μm, and especially not more than 8 μm. The MMAD of the fine excipient particles will generally be not less than 0.1 μm, for example not less than 1 μm. Advantageously the fine excipient particles are present in an amount of up to 50%, for example from 0.1 to 20%, and preferably from 1 to 15%, by weight based on the total weight of the formulation.

Where fine excipient particles are present, they may be present in an amount of up to 99% by weight of the total weight of fine excipient particles and additive material. Advantageously, fine excipient particles are present in an amount of at least 30%, preferably at least 50% and especially at least 90% by weight, based on the total weight of fine excipient particles and additive material. The fine excipient particles and additive material, advantageously constitute from 5%, or from 10% to two thirds by weight of the total weight of fine excipient particles, additive material and carrier particles.

Where, as is preferred, the carrier particles and the fine excipient particles are of the same compound, for example, lactose, it may be found convenient to consider all the particles of that compound having an aerodynamic diameter of less than 50 μm to be fine excipient particles, whilst particles of aerodynamic diameter of 50 μm or more are regarded as carrier particles.

The advantageous flow properties of formulations of the invention may be demonstrated, for example, using a Flodex Tester, which can determine a flowability index over a scale of 4 to 40 mm, corresponding to a minimum orifice diameter through which smooth flow of the formulation occurs in the Tester. The flowability index, when so measured, of formulations of the invention containing fissured lactose will generally be below 12 mm, even where fine particle contents (that is, particles of aerodynamic diameter less than 50 μm or preferably less than 20 μm) exceed 10% by weight of the formulation.

The invention provides a formulation for use in a dry powder inhaler, comprising more than 5%, preferably more than 10% by weight, based on the total weight of the formulation, of particles of aerodynamic diameter less than 20 μm, the formulation having a flowability index of 12 mm or less. The term "flowability index" as used herein refers to flowability index values as measured using a Flodex Tester.

In addition to the carrier particles, active particles and fine excipient particles, the formulation may comprise one or more further additives suitable for use in inhaler formulations, for example, flavourings, lubricants, and flow improvers. Where such further additives are present, they will generally not exceed 10% by weight of the total weight of the formulation.

The formulations of the invention may be made by combining the components in any suitable manner. In a preferred method, however, the formulations are made by mixing the additive and fine excipient particles in a high energy mixing step, mixing the composite particles so obtained with the carrier particles, and adding to the mixture so obtained the at least one active ingredient. In another advantageous method, additive particles and excipient particles are co-micronised so as to significantly reduce their particle size, the co-micronised particles are mixed with the carrier particles, and the at least one active ingredient is added to the mixture so obtained. Suitable mixers for carrying out a high energy mixing step in the context of such formulations are high shear mixers. Such mixers are known to those skilled in the art, and include, for example, the Cyclomix and the Mechano-Fusion mixers manufactured by Hosokawa Micron. It will be appreciated by those skilled in the art that other suitable apparatus for use in a high energy mixing step will include, for example, ball mills and jet mills, provided that the equipment and conditions are so arranged to effect the desired high energy mixing.

The formulation may be a powder formulation for use in a dry powder inhaler. The formulation may be suitable for use in a pressurised metered dose inhaler.

One embodiment of the invention will now be described in detail with reference to the accompanying illustrations in which:

FIG. 1 is a scanning electron micrograph (SEM) of a relatively highly fissured lactose particle;

FIG. 2 is an SEM at lower magnification than FIG. 1 showing a number of lactose particles;

FIG. 3 is an SEM of a lactose carrier particle loaded with leucine and salbutamol sulphate; and FIG. 4 is an SEM of a formulation containing conventional lactose carrier particles and fine excipient particles.

With reference to FIG. 1, it may be seen that the lactose carrier particle consists of a number of individual lactose crystals which are fused to one another. The crystals define between them at the surface of the particle a multiplicity of relatively deep fissures or crevices. Such particles are known and have previously been regarded as suitable for use in tablet manufacture. Surprisingly, it has been found that carrier particles such as that shown in FIG. 1 are able to enhance the fine particle fraction of an active substance in the presence of additive. The active substance, together with the fine excipient, tend because of their small particle size and consequent high surface energy to adhere to the carrier particles. Adhesion occurs predominantly within the fissures and crevices. Due to the optimum width, depth and shape of the fissures, the resultant loaded carrier particles have good stability against deagglomeration within the inhaler device and yet permit effective dispersion of the active particles and fine excipient on expulsion from the device after actuation.

FIG. 2 shows a group of carrier particles similar to that of FIG. 1.

Referring to FIGS. 3 and 4, the lactose carrier particle of FIG. 3 holds the fine material, consisting of leucine as additive material and salbutamol sulphate as active material, within the fissures of its agglomerated structure to form a relatively cohesive structure, whilst in the conventional formulation of FIG. 4 much of the fine material is not adhered to the lactose carrier particles. The conventional carrier particles are typically crystals which have the characteristic tomahawk shape of lactose crystals. They may also be amorphous in shape, but rarely consist of more than two fused crystals. Thus the conventional carrier particles are substantially without the clefts and valleys of the fissured particles used in accordance with the present invention.

References herein to a "diameter" in relation to carrier particles means the diameter determined using laser diffraction, for example, using a Malvern Mastersizer, and references herein to a "mass median diameter" in relation to carrier particles is to be interpreted accordingly.

It may be found convenient to determine the diameters of particles in a formulation according to the invention by dispersing the particles in a liquid that does not dissolve any of the component particles, sonicating to ensure complete dispersion, and analysing the dispersion by means of laser diffraction, for example using a Malvern Mastersizer. That method will be suitable where separate analysis of fine particles of different materials is unnecessary.

In practice, it may be desired to examine a larger particle size fraction separately from a smaller size fraction. In that case, an air jet sieve may be used to effect separation. A mesh corresponding to the desired diameter at which the separation is to be effected is then used in the air jet sieve. A mesh corresponding to a diameter of 50 µm may thus be used for separation, larger particles being retained by the sieve whilst smaller particles pass through to be collected on a filter. That enables different techniques to be applied to analysis of the larger particles ($\geq$50 µm) and the smaller particles (<50 µm) if desired.

In the case of particles of the size of the carrier particles used in accordance with the invention, the diameter as measured using laser diffraction approximates the aerodynamic diameter. If preferred, therefore, the aerodynamic diameters of the carrier particles may be determined and the mass median aerodynamic diameter (MMAD) calculated therefrom.

MMADs referred to herein in relation to additive materials, fine excipient particles and active particles may be measured using any suitable technique, for example, using an impactor such as a cascade impactor, and analysing the size fractions so obtained, for example using HPLC.

Alternatively, respective samples of the formulation may each be treated with a solvent that is known to disolve one or more, but not all, of the ingredients and examining the undisolved particles by any suitable method, for example, laser diffraction.

The following Examples illustrate the invention.

EXAMPLE 1

20 g of Microfine lactose (Burculo—MMAD about 8 µm) and 0.4 g of L-leucine (Ajinomoto) were combined and placed in a stainless steel ball mill, filled with stainless steel balls of varying diameter to approximately 50% of the mill volume. The mill was rotated at approximately 60 RPM for about 120 minutes. The milled material (MMAD about 5 µm) was then recovered from the mill and from the surface of the balls, and is referred to below as the fines.

8 g of sieved Prismalac lactose was weighed into a glass vessel. Prismalac (trade mark) lactose is sold in the UK by Meggle for use in tablet manufacture. The lactose, as purchased, had been sieved on a stack of sieves in order to recover the sieve fraction passing through a 600 µm mesh sieve, but not passing through a 355 µm mesh sieve. That fraction is referred to below as 355-600 Prismalac and has a mean tapped density of 0.49 g/cm$^3$ and a bulk density as measured by mercury intrusion porosimetry of 0.47 g/cm$^3$.

1 g of the fines obtained as described above, and 1 g of micronised salbutamol sulphate (MMAD~2 µm) was added to the 355-600 Prismalac in the glass vessel. The glass vessel was sealed and the vessel located in a "Turbula" tumbling blender. The vessel and contents were tumbled for approximately 30 minutes at a speed of 42 RPM.

The formulation so obtained was loaded into size 3 gelatin capsules at 20 mg per capsule. The loaded capsules were rested for a period of 24 hours. Three capsules were then fired sequentially into a Twin Stage Impinger from a Cyclohaler at a flow rate of 60 liters per minutes, with a modified stage 1 jet of 12.5 mm internal diameter, which was estimated to produce a cut-off diameter of 5.4 µm. The operation of the Twin Stage Impinger is described in WO95/11666. Modification of a conventional Twin Stage Impinger, including the use of modified stage 1 jets, is described by Halworth and Westmoreland (J. Pharm. Pharmacol. 1987, 39:966-972).

TABLE 1

|  | Example 1 | Comparison 1 | Comparison 2 |
|---|---|---|---|
| 355-600 Prismalac lactose | 8 g 80% | 8 g | 4 g |
| Salbutamol sulphate | 1 g 10% | 1 g | 0.5 g |
| Microfine lactose | 0.9804 g 9.804% | — | 0.5 g |
| Leucine | 0.0196 g 0.196% |  | — |
| Fine particle fraction | 50% | 10% | 40% |

The composition of the formulation is summarised in Table 1 above.

As shown in Table 1, the fine particle fraction is improved in the presence of added fine lactose (Comparison 2) as compared with a formulation which contains no added fine lactose (Comparison 1). The best performance is obtained from the formulation according to the invention, containing leucine as well as fine lactose. On omission of the Prismalac from the ingredients of Example 1, the formulation was found to have very poor flow properties, preventing reliable and reproducible metering. As a result, the fine particle fraction was found to be very variable.

EXAMPLE 2

Example 1 was repeated using micronised budesonide (MMAD 2 µm) in place of salbutamol sulphate, and magnesium stearate in place of leucine. The results are summarised in Table 2, which also indicates the amounts of each ingredient.

TABLE 2

| 355-600 Prismalac lactose | 4 g | 80% |
|---|---|---|
| Budesonide | 0.5 g | 10% |
| Microfine lactose | 0.45 g | 9% |
| Magnesium stearate | 0.05 g | 1% |
| Fine particle fraction |  | 40% |

EXAMPLE 3

Example 1 was repeated using Prismalac lactose which had been sieved, the sieve fractions of 212 to 355 µm (with mean tapped density 0.65 g/cm$^3$ and a bulk density as measured by mercury instrusion porosimetry of 0.57 g/cm$^3$) being recovered and used instead of the 355-600 Prismalac lactose used in Example 1. Once again, a fine particle fraction of about 50% was obtained.

EXAMPLE 4

Example 1 was repeated replacing the leucine by one of the following: lecithin, stearylamine, magnesium stearate, and sodium stearyl fumarate.

The results are summarised in Table 3.

TABLE 3

| Additive | Fine particle fraction |
| --- | --- |
| Lecithin | 50% |
| Stearylamine | 50% |
| Purified phosphatidyl cholines | 35% |
| Sodium stearyl fumarate | 40% |

EXAMPLE 5

Micronised salbutamol sulphate was mixed with 5% by weight of sublimed L-leucine in a blender. The mixture so obtained was then tumbled in the ratio of 1:6 with Prismalac (355 to 600 μm fraction) for 15 minutes. The fine particle fraction, determined using a Twin Stage Impinger modified as described in Example 1, was 65%.

EXAMPLE 6

95 g of Microfine lactose (Borculo) was placed in a ceramic milling vessel (manufactured by the Pascall Engineering Company). 5 g of additive material (L-leucine) and the ceramic milling balls were added. The ball mill was tumbled at 60 rpm for 5 hours. The powder was recovered by sieving to remove the milling balls.

0.9 g of the composite excipient particles so obtained containing 5% l-leucine in Microfine lactose was blended with 0.6 g of budesonide by hand in a mortar. This blending could also be performed, for example, in a high shear blender, or in a ball mill or in a centrifugal mill. 20 parts by weight of this powder were blended with 80 parts by weight of a coarse carrier lactose (sieve-fractionated Prismalac—355 to 600 μm fraction) by tumbling. The powder was fired from a Cyclohaler at a flow rate of 60 l/minute in a multi-stage liquid impinger. The fine particle fraction (<approx. 5 μm) was 45%.

EXAMPLE 7

98 g of Microfine (MMAD approximately 8 μm) lactose (manufactured by Borculo) was placed in a stainless steel milling vessel. 300 g of stainless steel milling balls varying from 10 to 3 mm diameter were added. 2 g of lecithin was added and the vessel was located in a Retsch S100 Centrifugal Mill. The powder was milled for 30 minutes at 580 rpm and was then sieved to remove the milling balls.

1 g of salbutamol sulphate was added to 1 g of the composite excipient particles so obtained containing 2% lecithin, and to 8 g of sieve-fractionated Prismalac lactose (355 to 600 μm fraction). The mixture was tumbled for 30 minutes at 42 rpm. The resulting powder was fired from a Cyclohaler at a flow rate of 60 liters per minute into a twin-stage impinger, giving a fine particle fraction (<approx. 5 μm) of about 44%. A similar example with a 2% leucine precursor gave a fine particle fraction (<approx. 5 μm) of 52%.

Other additive materials that may be used instead of lecithin to form composite excipient particles as described above are: magnesium stearate, calcium stearate, sodium stearate, lithium stearate, stearic acid, stearylamine, soya lecithin, sodium stearyl fumarate, l-leucine, l-isoleucine, oleic acid, starch, diphosphatidyl choline, behenic acid, glyceryl behenate, and sodium benzoate. Pharmaceutically acceptable fatty acids and derivatives, waxes and oils may also be used.

EXAMPLE 8

10 g of Microfine lactose (Borculo) was combined with 1 g of magnesium stearate and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate was added to 0.5 g of the composite excipient particles so obtained containing magnesium stearate, and to 4 g of sieve-fractionated Prismalac lactose (355-600 μm fraction). This was tumbled for 30 minutes at 62 rpm. The resulting powder was fired from a Cyclohaler at a flow rate of 60 liters per minute into a twin-stage impinger, giving a fine particle fraction (<approx. 5 μm) of 57%. The experiment was repeated using composite excipient particles containing 20% magnesium stearate and similar results were obtained.

EXAMPLE 9

10 g of Microfine lactose (Borculo) was combined with 1 g of leucine and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate, 0.25 g of composite excipient particles made as described in Example 8 containing magnesium stearate, 0.25 g of composite excipient particles made as described above containing leucine, and 4 g of sieve-fractionated Prismalac (355-600 μm fraction) were all combined. The mixture was tumbled for 30 minutes at 62 rpm. The resulting powder was fired from a Cyclohaler at a flow rate of 60 liters per minute into a twin-stage impinger, giving a fine particle fraction (<approx. 5 μm) of 65%.

EXAMPLE 10

10 g of Microfine lactose (Borculo) was combined with 1 g of lecithin and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate was added to 0.25 g of the composite excipient particles so obtained containing lecithin, 0.25 g of composite excipient particles made as described in Example 9 containing leucine, and 4 g of sieve-fractionated Prismalac lactose (355-600 μm fraction). The mixture was tumbled for 30 minutes at 62 rpm. The resulting powder was fired from a Cyclohaler at a flow rate of 60 liters per minute into a twin-stage impinger, giving a fine particle fraction (<approx. 5 μm) of 68%.

EXAMPLE 11

95 g Sorbolac 400 (Meggle) were combined with 5 g of magnesium stearate and 50 ml dichloromethane and milled in a Retsch S100 centrifugal mill with 620 g of 5 mm stainless steel balls in a stainless steel vessel for 90 minutes at 500 rpm. The powder was recovered after evaporation of the dichloromethane by briefly milling (1 minute) and subsequent sieving. 10 g of the composite excipient/additive particles so obtained were added to 89.5 g of sieve fractionated Prismalac lactose (355-600 μm fraction). The mixture was tumbled for 30 minutes at 60 rpm, then 0.5 g budesonide was added and tumbling continued for a further 30 minutes at 60 rpm. The powder was fired from a Cyclohaler at 60 l/minute into a Twin-Stage Impinger, and gave a fine particle fraction (<approx. 5 μm) of about 80%.

EXAMPLE 12

(a) A pre-blend was made by milling an additive material and microfine lactose (<20 micron) together in a ball mill. Then 1 g of the pre-blend, 1 g of salbutamol sulphate and 8 g of coarse lactose (Prismalac 355-600 μm fraction) were mixed together in a glass vessel in a Turbula mixer at 42 rpm to create the final formulation. Size 2 capsules were filled with 20 mg of the formulation. For each test, 3 capsules were fired into a 'rapid TSI' from a cyclohaler giving a total delivered dose of 6 mg of salbultamol sulphate per test. The additive material was selected from lithium stearate, calcium stearate, magnesium stearate, sodium stearate, sodium stearyl fumarate, leucine, lecithin and stearylamine.

(b) The method of (a) above was repeated using leucine, except that the pre-blend was mixed with the coarse lactose in a glass vessel shaken by hand.

The "rapid TSI" is a modified methodology based on a conventional TSI. In the rapid TSI the second stage of the impinger is replaced by a glass fibre filter (Gelman A/E, 76 mm). This enables the fine particle fraction of the formulation (i.e. particles with an MMAD<5 μm) to be collected on a filter for analysis. Analysis was conducted by sonicating the filter in a 0.06M NaOH solution and analysed at 295 nm on a UV spectrophotomer (Spectronic 601). The fine particle fraction corresponds substantially to the respirable fraction of the formulation.

Further details of the formulations and the % fine particle fraction estimated using the "rapid TSI" method described above are given in Table 4 below.

Segregation has not been observed in the above formulations, even those comprising 10 and 20% magnesium stearate (i.e. up to 2% in the final composition).

The above processes have been applied to a variety of active materials. When the active material is a protein, the milling may be preceded by lyophilisation (freeze drying) of the protein either pure or in combination with an additive material and/or a polymeric stabiliser. The freeze drying may make the protein more brittle and more easily milled. The milling may need to be conducted under cryogenic (cold) conditions to increase the brittleness of the material.

TABLE 4

| Additive Material ("AM") | % AM in pre-blend | % AM in formulation | Mass (mg) SaS04 | Estimated % FPF | Pre-blend mill method |
|---|---|---|---|---|---|
| Lithium St | 2 | 0.2 | 2.549 | 42 | 30 mins |
| | | | 2.763 | 46 | |
| Calcium St | 2 | 0.2 | 2.721 | 45 | 1 hr |
| | | | 2.633 | 44 | |
| Magnesium St | 2 | 0.2 | 2.108 | 35 | 1 hr |
| | | | 2.336 | 39 | |
| Sodium St | 2 | 0.2 | 3.218 | 54 | 30 mins |
| | | | 3.153 | 53 | |
| Sodium stearyl | 2 | 0.2 | 2.261 | 38 | 30 mins |
| Fumarate | | | 2.113 | 35 | |
| Leucine | 2 | 0.2 | 2.429 | 40 | 2 hrs |
| | | | 2.066 | 34 | |
| Leucine | 2 | 0.2 | 2.136 | 36 | 2 hrs |
| [12 (b)] | | | 2.600 | 43 | |
| Leucine | 5 | 0.5 | 2.782 | 46 | 30 mins |
| | | | 3.000 | 50 | |
| Leucine | 5 | 0.5 | 2.772 | 46 | |
| | | | 2.921 | 49 | 5 hrs |
| Magnesium St | 5 | 0.5 | 2.438 | 41 | 30 mins |
| | | | 2.721 | 45 | |
| Lecithin | 2 | 0.2 | 3.014 | 50 | 30 mins |
| | | | 2.884 | 48 | |
| Stearylamine | 2 | 0.2 | 2.847 | 47 | 30 mins |
| | | | 3.037 | 51 | |

EXAMPLE 13

Determination of the suitable amount of magnesium stearate to be added in the formulation.

Samples of pre-blends were prepared by co-milling in a ball milling apparatus for 2 hours α-lactose monohydrate SorboLac 400 (Meggle microtose) with a starting particle size below 30μ(d(v, 0.5) of about 10 μm) and magnesium stearate with a starting particle size of 3 to 35 μm (d(v, 0.5) of about 10 μm) in the ratio 98:2, 95:5 and 90:10% by weight (blends A).

85% by weight of α-lactose monohydrate CapsuLac (212-355 μm) was placed in a 240 ml stainless steel container, then 15% by weight of a respective blend A was added. The blend was mixed in a Turbula mixer for 2 hours at 42 rpm (blend B). Micronised formoterol fumarate was added to the blend B and mixed in a Turbula mixer for 10 mins at 42 rpm to obtain a ratio of 12 μg of active to 20 mg of carrier. The final formulation (hard pellet formulation) was left to stand for 10 mins then transferred to an amber glass jar.

The amount of magnesium stearate in the final formulations turns out to be 0.3, 0.75 and 1.5% by weight, respectively. The uniformity of distribution of active ingredient and the in-vitro aerosol performance were determined as follows:

a) The uniformity of distribution of the active ingredient was evaluated by withdrawing 10 samples, each equivalent to about a single dose, from different parts of the blend. The amount of active ingredient of each sample was determined by High-Performance Liquid Chromatography (HPLC).

b) Determination of the aerosol performances.

An amount of powder for inhalation was loaded in a multidose dry powder inhaler (Pulvinal®—Chiesi Pharmaceutical SpA, Italy).

The evaluation of the aerosol performances was performed by using a modified Twin Stage Impinger apparatus, TSI (Apparatus of type A for the aerodynamic evaluation of fine particles described in FU IX, 4° supplement 1996). The equipment consists of two different glass elements, mutually connected to form two chambers capable of separating the powder for inhalation depending on its aerodynamic size; the chambers are referred to as higher (stage 1) and lower (stage 2) separation chambers, respectively. A rubber adaptor secures the connection with the inhaler containing the powder. The apparatus is connected to a vacuum pump which produces an air flow through the separation chambers and the connected inhaler. Upon actuation of the pump, the air flow carries the particles of the powder mixture, causing them to deposit in the two chambers depending on their aerodynamic diameter. The apparatus used were modified in the Stage 1 Jet in order to obtained an aerodynamic diameter limit value, dae, of 5 µm at an air flow of 30 l/min, that is considered the relevant flow rate for Pulvinal® device. Particles with higher dae deposit in Stage 1 and particles with lower dae in Stage 2. In both stages, a minimum volume of solvent is used (30 ml in Stage 2 and 7 ml in Stage 1) to prevent particles from adhering to the walls of the apparatus and to promote the recovery thereof.

The determination of the aerosol performances of the mixture obtained according to the preparation process a) was carried out with the TSI applying an air flow rate of 30 l/min for 8 seconds.

After nebulization of 10 doses, the Twin Stage Impinger was disassembled and the amounts of drug deposited in the two separation chambers were recovered by washing with a solvent mixture, then diluted to a volume of 100 and 50 ml in two volumetric flasks, one for Stage 1 and one for Stage 2, respectively. The amounts of active ingredient collected in the two volumetric flasks were then determined by High-Performance Liquid Chromatography (HPLC). The following parameters, were calculated: i) the shot weight expressed as mean and relative standard deviation (RSD) ii) the fine particle dose (FPD) which is the amount of drug found in stage 2 of TSI; iii) the emitted dose which is the amount of drug delivered from the device recovered in stage 1+stage 2; iv) the fine particle fraction (FPF) which is the percentage of the emitted dose reaching the stage 2 of TSI.

TABLE 5

Uniformity of distribution and in-vitro aerosol performances

|  | Mg stearate 0.3% | Mg stearate 0.75% | Mg stearate 1.5% |
|---|---|---|---|
| Content uniformity | | | |
| Mean (µg) | 11.84 | — | — |
| RSD (%) | 1.83 | — | — |
| Shot weight | | | |
| Mean (mg) | 20.8 | 24.7 | 23.0 |
| | 4.28 | | |
| | 49.9 | | |
| RSD (%) | 6.9 | 6.5 | 2.4 |

TABLE 5-continued

Uniformity of distribution and in-vitro aerosol performances

|  | Mg stearate 0.3% | Mg stearate 0.75% | Mg stearate 1.5% |
|---|---|---|---|
| Emitted dose (µg) | 8.57 | 10.1 | 11.1 |
| FPD (µg) | 4.28 | 3.5 | 3.6 |
| FPF (%) | 49.9 | 35 | 32 |

In all cases, good performances in terms of fine particle dose are obtained, in particular with 0.3% by weight of magnesium stearate in the final formulation.

EXAMPLE 14

Effect of the Addition of Magnesium Stearate By Simple Mixing

Formulation A—α-Lactose monohydrate Pharmatose 325M (30-100 µm) and magnesium stearate in the ratio 99.75:0.25% by weight were blended in a Turbula mixer for 2 hours at 42 rpm. The blend was mixed with formoterol fumarate in a Turbula mixer for 30 mins at 42 rpm to obtain a ratio of 12 µg of active to 25 mg of carrier.

Formulation B—as reported above but α-Lactose monohydrate SpheroLac 100 (90-150 µm) was used instead of Pharmatose 325M.

Formulation C—α-Lactose monohydrate PrismaLac 40 (with a particle size below 355 µm) and micronised lactose with a particle size below 5 µm in the ratio 40:60% by weight were mixed in a Turbula mixer for 60 mins at 42 rpm 99.75% by weight of the resulting blend and 0.25% by weight of magnesium stearate were mixed in a Turbula mixer for 60 mins at 42 rpm. The resulting blend was finally mixed with formoterol fumarate in a Turbula mixer for 30 mins at 42 rpm to obtain a ratio of 12 µg of active to 15 mg of carrier.

Formulation D—Sorbolac 400 with a particle size below 30 µm (d(v, 0.5) of about 10 µm) and magnesium stearate in the ratio 98:2% by weight were mixed in a high shear mixer for 120 mins (blend A). 85% by weight α-lactose monohydrate CapsuLac (212-355 µm) and 15% by weight of blend A were mixed in Turbula for 2 hours at 42 rpm (blend B); the amount of magnesium stearate in the final formulation is 0.3% by weight. Micronised formoterol fumarate was placed on the top of blend B and mixed in a Turbula mixer for 10 mins at 42 rpm to obtain a ratio of 12 µg of active to 20 mg of carrier.

Formulation E—Micronized lactose with a particle size below 10 µm (d(v, 0.5) of about 3 µm) and magnesium stearate in the ratio 98:2% by weight were mixed in a Sigma Blade mixer for 60 mins (blend A). 85% by weight of α-lactose monohydrate CapsuLac (212-355 µm) and 15% by weight of blend A were mixed in Turbula for 2 hours at 42 rpm (blend B); the amount of magnesium stearate in the final formulation is 0.3% by weight. Micronised formoterol fumarate was placed on the top of blend B and mixed in a Turbula mixer for 10 mins at 42 rpm to obtain a ratio of 12 µg of active to 20 mg of carrier.

The results in terms of uniformity of distribution of active ingredient and in-vitro aerosol performances were determined as described in Example 13 and are reported in Table 6.

TABLE 6

Uniformity of distribution of active ingredient and in-vitro aerosol performances

|  | Formulations A | Formulations B | Formulations C | Formulations D | Formulations E |
|---|---|---|---|---|---|
| Content uniformity | | | | | |
| Mean (μg) | 7.96 | 10.50 | 9.10 | 10.68 | 11.32 |
| RSD (%) | 2.16 | 8.30 | 24.90 | 2.80 | 3.0 |
| Shot weight | | | | | |
| Mean (mg) | 24.10 | 26.50 | 12.50 | 22.07 | 21.87 |
| RSD (%) | 34.60 | 8.20 | 15.30 | 2.50 | 4.0 |
| Emitted dose (μg) | 6.10 | 7.60 | 9.60 | 8.60 | 9.93 |
| FPD (μg) | 0.60 | 0.90 | 1.60 | 3.38 | 4.80 |
| FPF (%) | 9.8 | 11.8 | 16.7 | 39.3 | 48.37 |

Formulations where magnesium stearate is added by a high energy mixing to a small amount of fine lactose (blend A of the formulations D and E), and combined with a 212-355 μm coarse lactose fraction, show a significant increase in performance. In addition, the particle size of the fine lactose used has a significant effect on the deaggregation properties of the final formulation; in fact, formulation E prepared using a micronized lactose shows a significant improved performance compared with formulation D.

EXAMPLE 15

Effect of the Amount of Micronized Pre-blend in the Final Formulation

α-Lactose monohydrate SpheroLac 100 (Meggle EP D30) with a starting particle size of 50 to 400 μm (d(v, 0.5) of about 170 μm and magnesium stearate with a starting particle size of 3 to 35 μm (d(v, 0.5) of about 10 μm) in the ratio 98:2% by weight were co-milled in a jet mill apparatus (blend A) Different ratios of α-lactose monohydrate Capsulac (212-355 μm) and blend A were placed in a stainless steel container and mixed in a Turbula mixer for four hours at 32 rpm (blends B).

Micronised formoterol fumarate was placed on the top of blends B and mixed in a Turbula mixer for 30 mins at 32 rpm to obtain a ratio of 12 μg of active to 20 mg total mixture. The amount of magnesium stearate in the final formulation ranges between 0.05 and 0.6% by weight.

The results in terms of uniformity of distribution of active ingredient and in-vitro aerosol performances were determined as in Example 13 and are reported in Table 7.

TABLE 7

Uniformity of distribution of active ingredient and in-vivo aerosol performance

|  | Ratio 97.5:2.5 | Ratio 95:5 | Ratio 92.5:7.5 | Ratio 90:10 | Ratio 80:20 | Ratio 70:30 |
|---|---|---|---|---|---|---|
| Content uniformity | | | | | | |
| Mean (g) | 11.29 | 12.25 | 11.53 | 11.93 | 11.96 | 12.00 |
| RSD (%) | 3.8 | 5.7 | 1.5 | 2.5 | 2.0 | 2.0 |
| Shot weight | | | | | | |
| Mean (mg) | 19.27 | 20.26 | 20.38 | 21.05 | 22.39 | 22.48 |
| RSD (%) | 4.7 | 3.3 | 3.2 | 4.3 | 3.5 | 3.7 |
| Emitted dose (μg) | 10.58 | 9.20 | 10.65 | 9.18 | 9.63 | 9.88 |
| FPD (μg) | 4.18 | 5.10 | 6.78 | 5.9 | 5.33 | 5.28 |
| FPF (%) | 39.4 | 55.4 | 63.6 | 64.3 | 55.3 | 53.4 |

The results indicate that the performances of all the formulations are good.

EXAMPLE 16

10 g of the composite excipient particles containing 5% magnesium stearate obtained in accordance with Example 11 were mixed with 89.5 g coarse lactose (Prismalac; 355-600 μm fraction) in a Turbula mixer for 30 minutes. 0.5 g micronised dihydroergotamine mesylate was added and mixing continued in the Turbula for a further 30 minutes. The powder was fired from a Cyclohaler into a Multi-Stage Liquid Impinger (Apparatus C, European Pharmacopoeia, Method 5.2.9.18, Supplement 2000), and gave a fine particle fraction (<approx. 5 μm) of about 60%.

EXAMPLE 17

Composite excipient particles were manufactured by milling 95 g fine lactose (Sorbolac 400—Meggle) with 5 g magnesium stearate and 50 ml dichloromethane in a Retsch S100 centrifugal mill with 620 g of 5 mm stainless steel balls in a stainless steel vessel for 90 minutes at 500 rpm. The powder was recovered after evaporation of the dichloromethane by briefly milling (1 minute) and subsequent sieving. 10 g of the composite excipient/additive particles so obtained were added to 89.5 g of sieve fractionated Prismalac lactose (355-600 μm fraction). The mixture was tumbled in a Turbula mixer for 30 minutes at 60 rpm, then 0.5 g fentanyl citrate was added and tumbling continued for a further 30 minutes at 60 rpm. The powder so obtained was fired from a Cyclohaler at 60 l/min into a Twin-Stage Impinger, and gave a fine particle fraction (<approx. 5 μm) of about 50%.

EXAMPLE 18

Various formulations, each combining 89.5 g, 10 g composite excipient particles and 0.5 g budesonide were made according to the method of Example 11.

Their flowabilities were then measured using a FLODEX (trade mark) tester, made by Hanson Research. The FLODEX provides an index, over a scale of 4 to 40 mm, of flowability of powders. Analysis was conducted by placing 50 g of formulation into the holding chamber of the FLODEX via a funnel, allowing the formulation to stand for 1 minute, and then releasing the trap door of the FLODEX to open an orifice at the base of the holding chamber. Orifice diameters of 4 to 34 mm were used to measure the index of flowability. The flowability of a given formulation is determined as the smallest orifice diameter through which flowing of the formulation is smooth.

The results are shown in Table 8.

Comparison data is given for a formulation made by mixing for 30 minutes in a Turbula mixer 45 g Pharmatose 325M lactose (a lactose used in certain conventional formulations) and 5 g microfine lactose.

TABLE 8

| Carrier particles | Composite particles | Flowability |
|---|---|---|
| Prismalac 355-600 | Leucine:Sorbolac400 1:9 | <4 mm |
| Prismalac 355-600 | Lecithin:Sorbolac400 1:9 | <4 mm |
| Prismalac 355-600 | Magnesium stearate:Sorbolac400 1:19 | <4 mm |
| Prismalac 355-600 | Magnesium stearate:microfine lactose 1:19 | <4 mm |
| Pharmatose 325M | Microfine lactose | <34 mm |

The results in Table 8 illustrate the excellent flowability of the formulations according to the invention.

COMPARISON EXAMPLE 1

99.5 g of sieve-fractionated Prismalac (355-600 μm fraction) was tumbled with 0.5 g budesonide for 30 minutes at 60 rpm. The powder, fired from a Cyclohaler at 90 liters per minute into a Multi-Stage Liquid Impinger gave a fine particle fraction (<approx. 5 μm) of about 30%.

The invention claimed is:

1. A formulation for use in an inhaler device, comprising:
carrier particles in the form of an agglomerate consisting of a plurality of crystals fused to one another via solid bridges such that the particles have no tendency to disintegrate on expulsion from the inhaler device, wherein the carrier particles have a diameter of at least 50 μm and a mass median diameter of at least 175 μm and a fissured surface, wherein the fissures are at least 20 μm wide and at least 20 μm deep;
pharmaceutically active particles; and
composite particles comprising additive material and fine excipient material consisting of one or more crystalline sugars, prepared as a pre-blend prior to the addition of the active and carrier particles by milling or high-energy mixing the additive and fine excipient material;
wherein the additive material includes one or more compounds selected from amino acids and derivatives thereof; peptides and polypeptides having a molecular weight from 0.25 to 1000 Kda, and derivatives thereof; phospholipids or a derivative thereof; fatty acids and derivatives thereof; or a surface active material.

2. A formulation according to claim 1, in which the mass median diameter of the carrier particles is at least 200 μm.

3. A formulation according to claim 1, in which the carrier particles are of a crystalline sugar.

4. A formulation according to claim 3, in which the carrier particles are of dextrose or lactose.

5. A formulation according to claim 4, in which the carrier particles are of lactose.

6. A formulation according to claim 1, in which the carrier particles are of a crystalline sugar having a tapped density not exceeding 0.75 g/cm$^3$.

7. A formulation according to claim 6, in which the carrier particles have a tapped density not exceeding 0.7 g/cm$^3$.

8. A formulation according to claim 1, in which the carrier particles have a bulk density as measured by mercury intrusion porosimetry of not exceeding 0.6 g/cm$^3$.

9. A formulation according to claim 1, in which the carrier particles are obtainable by a wet granulation process.

10. A formulation according to claim 1, in which the carrier particles are dendritic spherulites.

11. A formulation according to claim 1, in which the additive material is present in an amount of not more than 50% by weight based on the total weight of the formulation.

12. A formulation according to claim 11, in which the additive material is present in an amount of not more than 10% by weight based on the total weight of the formulation.

13. A formulation according to claim 12, in which the additive material is present in an amount of not more than 5% by weight based on the total weight of the formulation.

14. A formulation according to claim 1, in which the additive material includes one or more compounds selected from amino acids and derivatives thereof, and peptides and polypeptides having a molecular weight from 0.25 to 1000 Kda, and derivatives thereof.

15. A formulation according to claim 14, in which the additive material comprises an amino acid.

16. A formulation according to claim 15, in which the additive material consists essentially of leucine.

17. A formulation according to claim 1, in which the additive material comprises a phospholipid or a derivative thereof.

18. A formulation according to claim 17, in which the additive material comprises soya lecithin.

19. A formulation according to claim 1, in which the additive material comprises one or more compounds selected from the group consisting of magnesium stearate, calcium stearate, sodium stearate, lithium stearate, stearic acid, stearylamine, sodium stearyl fumarate, oleic acid, behenic acid, and glyceryl behenate.

20. A formulation according to claim 19, in which the additive is magnesium stearate.

21. A formulation according to claim 1, in which the additive material is selected from fatty acids and derivatives.

22. A formulation according to claim 1, in which the additive material is in particulate form.

23. A formulation according to claim 22, in which at least 90% by weight of the additive particles have an aerodynamic diameter of less than 100 μm.

24. A formulation according to claim 22, in which the mass median aerodynamic diameter of the additive particles is not more than about 10 μm.

25. A formulation according to claim 1, which comprises not less than 0.01% by weight of additive material based on the weight of the formulation.

26. A formulation according to claim 1, in which the additive material forms a discontinuous covering on the surfaces of the carrier particles.

27. A formulation according to claim 26, which contains up to 50% by weight of active particles, based on the total weight of active particles, additive material and carrier particles.

28. A formulation according to claim 1, which contains up to 90% by weight of active particles, based on the total weight of active particles, additive material and carrier particles.

29. A formulation according to claim 28, which contains up to 50% by weight of active particles, based on the total weight of active particles, additive material and carrier particles.

30. A formulation according to claim 29, which contains up to 20% by weight of active particles, based on the total weight of active particles, additive material and carrier particles.

31. A formulation according to claim 1, which comprises at least 50% by weight carrier particles, based on the total weight of the formulation.

32. A formulation according to claim 31, which comprises at least 70% by weight carrier particles, based on the total weight of the formulation.

33. A formulation according to claim 1, in which the active particles comprise one or more active agents selected from β$_2$-agonists, ipratropium bromide, steroids, cromones and leukotriene receptor antagonists and heparin.

34. A formulation according to claim 1, in which the active particles comprise a therapeutically active agent having systemic activity, the active agent being selected from DNase, leukotrienes, insulin, cyclosporin, interleukins, cytokines, anti-cytokines, cytokine receptors, vaccines, growth hormone, leuprolide and related analogues, interferons, desmopressin, immunoglobulins, erythropoeitin, calcitonin, parathyroid hormone, non-opioid analgesic agents and opioid analgesic agents.

35. A formulation according to claim 1, in which the active particles comprise one or more agents selected from peptides, polypeptides, proteins and DNA fragments.

36. A formulation according to claim 35, in which the active particles comprise insulin.

37. A formulation according to claim 1, wherein the fine excipient material comprises particles of an aerodynamic diameter of not more than 50 μm.

38. A formulation according to claim 37, in which the mass median aerodynamic diameter of the fine excipient particles is not more than 15 μm.

39. A formulation according to claim 38, in which the mass median aerodynamic diameter of the excipient particles is not more than 10 μm.

40. A formulation according to claim 37, which includes the fine excipient particles in an amount of not less than 4% by weight, based on the total weight of the formulation.

41. A formulation according to claim 37, including fine excipient particles in an amount of up to 20% by weight, based on the total weight of the formulation.

42. A formulation according to claim 41, in which the fine excipient particles are present in an amount of up to 15% by weight, based on the total weight of the formulation.

43. A formulation according to claim 37, in which the fine excipient particles are of dextrose or lactose.

44. A formulation according to claim 43, in which the fine excipient particles are of lactose.

45. A formulation according to claim 37, in which the carrier particles and the fine excipient particles are of the same material.

46. A formulation according to claim 37, comprising up to 20% by weight fine excipient particles and up to 10% by weight additive material, based on the total weight of the formulation.

47. A formulation according to claim 1, which comprises up to 10% by weight additive material, based on the total weight of the formulation.

48. A formulation according to claim 1, which comprises up to 5% by weight additive material, based on the total weight of the formulation.

49. A formulation according to claim 1, comprising more than 5%, by weight, based on the total weight of the formulation, of particles of aerodynamic diameter less than 20 μm, the formulation having a flowability index of 12 mm or less.

50. A formulation according to claim 1, comprising: from 5 to 90% by weight carrier particles having a diameter of at least 50 μm and a mass median diameter of at least 175 μm; from 0.01 to 90% by weight of a therapeutically active agent; from 0.01 to 50% by weight of an additive material; in each case, by weight, based on the total weight of the carrier particles, active agent and additive material; and fine excipient material in an amount of not more than 50% by weight, based on the total weight of the formulation.

51. A formulation according to claim 50, in which the carrier particles are present in an amount not exceeding 70% by weight, based on the total weight of the formulation.

52. A formulation according to claim 50 in which the total content of therapeutically active agent, additive material and fine excipient is at least 10% by weight based on the total weight of the formulation.

53. A formulation according to claim 52, in which the total content of therapeutically active agent, additive material and fine excipient particles, is at least 20% by weight, based on the total weight of the formulation.

54. An inhaler device comprising a formulation according to claim 1.

55. A device according to claim 54, which is a dry powder inhaler.

56. A device according to claim 54, which is a pressurised metered dose inhaler.

57. A method of manufacturing a formulation according to claim 1, comprising milling or high energy mixing the additive material with the fine excipient material, and mixing the resultant composite particles with the carrier particles and the active particles.

58. A method of increasing the fine particle fraction obtainable from a formulation for an inhaler device comprising:
pre-blending additive and fine excipient material consisting of one or more crystalline sugars by milling or high energy mixing to create composite particles, and then combining the composite particles with fissured carrier particles of mass median diameter of at least 175 μm wherein the additive material includes one or more compounds selected from amino acids and derivatives thereof; peptides and polypeptides having a molecular weight from 0.25 to 1000 Kda, and derivatives thereof; phospholipids or a derivative thereof; fatty acids and derivatives thereof; or a surface active material, and
wherein the carrier particles are in the form of an agglomerate consisting of a plurality of crystals fused to one another via solid bridges such that the particles have no tendency to disintegrate on expulsion from the inhaler device and have a fissured surface, wherein the fissures in the carrier particles are at least 20 μm wide and at least 20 μm deep.

59. A formulation according to claim 1, comprising more than 10% by weight, based on the total weight of the formulation, of particles of aerodynamic diameter less than 20 μm, the formulation having a flowability index of 12 mm or less.

60. A method according to claim 58, in which the additive material comprises an amino acid.

61. A method according to claim 60, wherein the additive material consists essentially of leucine.

62. A method according to claim 58, in which the additive material comprises one or more compounds selected from the group consisting of magnesium stearate, calcium stearate, sodium stearate, lithium stearate, stearic acid, stearylamine, sodium stearyl fumarate, oleic acid, behenic acid, and glyceryl behenate.

63. A method according to claim 62, in which the additive material is magnesium stearate.

* * * * *